US008334976B2

(12) United States Patent
Carney et al.

(10) Patent No.: US 8,334,976 B2
(45) Date of Patent: *Dec. 18, 2012

(54) SECOND-ORDER NONLINEAR SUSCEPTIBILITY OF A NANOPARTICLE USING COHERENT CONFOCAL MICROSCOPY

(75) Inventors: Paul Scott Carney, Urbana, IL (US); Kimani C. Toussaint, Champaign, IL (US); Brynmor J. Davis, Etna, NH (US); Santosh Tripathi, Kathmandu (NP)

(73) Assignee: The Board of Trustees of the University of Illinois, Urbana, IL (US)

( * ) Notice: Subject to any disclaimer, the term of this patent is extended or adjusted under 35 U.S.C. 154(b) by 42 days.

This patent is subject to a terminal disclaimer.

(21) Appl. No.: 13/154,014

(22) Filed: Jun. 6, 2011

(65) Prior Publication Data

US 2011/0267617 A1 Nov. 3, 2011

Related U.S. Application Data

(63) Continuation-in-part of application No. 12/405,711, filed on Mar. 17, 2009, now Pat. No. 8,045,161.

(60) Provisional application No. 61/037,419, filed on Mar. 18, 2008.

(51) Int. Cl.
*G01N 21/00* (2006.01)

(52) U.S. Cl. ................ 356/337; 356/336; 356/338

(58) Field of Classification Search .......... 356/335–342, 356/28.5, 301, 427; 250/281, 282, 292, 287–288, 250/484.4, 581, 584; 435/6; 977/786, 840
See application file for complete search history.

(56) References Cited

U.S. PATENT DOCUMENTS

| | | | |
|---|---|---|---|
| 4,410,237 A | 10/1983 | Veldkamp | 350/320 |
| 5,235,183 A | 8/1993 | Whiting et al. | 250/236 |
| 5,646,731 A * | 7/1997 | Wickramasinghe et al. | 356/498 |
| 6,682,596 B2 * | 1/2004 | Zehnder et al. | 117/68 |
| 7,119,331 B2 | 10/2006 | Chang et al. | 250/292 |
| 7,126,136 B2 * | 10/2006 | Chen | 250/484.4 |
| 7,324,280 B2 | 1/2008 | Albert | 359/489 |
| 7,372,562 B2 | 5/2008 | Islam et al. | 356/301 |
| 7,421,178 B2 | 9/2008 | Podolskiy et al. | 385/129 |
| 7,450,618 B2 | 11/2008 | Dantus et al. | 372/25 |
| 7,500,953 B2 * | 3/2009 | Oraevsky et al. | 600/458 |
| 7,528,959 B2 * | 5/2009 | Novotny et al. | 356/496 |
| 7,876,436 B2 | 1/2011 | Chu | 356/338 |
| 2004/0038264 A1 | 2/2004 | Souza et al. | 435/6 |
| 2006/0268408 A1* | 11/2006 | Toussaint et al. | 359/487 |
| 2011/0220799 A1* | 9/2011 | Kim et al. | 250/338.1 |

OTHER PUBLICATIONS

Abouraddy et al., "Three-Dimensional Polarization Control in Microscopy," *The American Physical Society (APS)*, Phys. Rev. Lett., vol. 96, No. 15, pp. 153901-1-153901-4 (Apr. 2006).

(Continued)

*Primary Examiner* — Sang Nguyen
(74) *Attorney, Agent, or Firm* — Sunstein Kann Murphy & Timbers LLP (57) ABSTRACT

A coherent confocal microscope and methods for measuring elements of the non-linear susceptibility of a nanoparticle, including, more particularly, all of the elements of the second-order susceptibility tensor of a single nanoparticle under permutation and Kleinman symmetry. Using a high numerical aperture lens, two-dimensional scanning and a vector beam shaper, the second-order nonlinear susceptibility is derived from a single confocal image. A forward model for the problem is presented and a computationally efficient data processing method robustly solves the inverse problem.

14 Claims, 5 Drawing Sheets

OTHER PUBLICATIONS

Beversluis et al., "Programmable vector point-spread function engineering," *Optics Express*, vol. 14, No. 7, pp. 2650-2656 (Apr. 2006).

Brasselet et al., "In-situ diagnostics of the crystalline nature of single organic nanocrystals by nonlinear microscopy," *The American Physical Society (APS)*, Phys. Rev. Lett., vol. 92, No. 207401, pp. 1-4 (May 2004).

Canfield et al., "Chirality arising from small defects in gold nanoparticle arrays," *Optics Express*, vol. 14, No. 2, pp. 950-955 (Jan. 2006).

Cooper et al., "Focusing of pseudoradial polarized beams," *Optics Express*, vol. 13, No. 4, pp. 1066-1071 (Feb. 2005).

Davis et al., "Nonparaxial vector-field modeling of optical coherence tomography and interferometric synthetic aperture microscopy," *J Opt. Soc. Am. A*, vol. 24, No. 9, pp. 2527-2542 (Sep. 2007).

Davis et al., "Spectral self-interference microscopy for low-signal nanoscale axial imaging," *J Opt. Soc. Am. A*, vol. 24, No. 11, pp. 3587-3599 (Nov. 2007).

DeCastro et al., "Registration of Translated and Rotated Images Using Finite Fourier Transforms," *IEEE Transactions on Pattern Analysis and Machine Intelligence*, vol. PAMI-9, No. 5, pp. 700-703 (Sep. 1987).

Failla et al., "Orientational Imaging of Subwavelength Au Particles with Higher Order Laser Modes," *American Chemical Society, Nano Lett.*, vol. 6, No. 7, pp. 1374-1378 (Jun. 2006).

Failla et al., "Topology measurements of metal nanoparticles with 1 nm accuracy by Confocal Interference Scattering Microscopy," *Optics Express*, vol. 15, No. 14, pp. 8532-8542 (Jul. 2007).

Hassey et al., "Probing the chiroptical response of a single molecule," *Science Magazine*, vol. 314, No. 5804 pp. 1439-1439 (Dec. 2006) [Abstract Only—1 page].

Ignatovich et al., "Real-Time and Background-Free Detection of Nanoscale Particles," *The American Physical Society (APS)*, Phys. Rev. Lett., vol. 96, No. 1, pp. 013901-1-013901-4 (Jan. 2006).

Kulzer et al., "Single-Molecule Optics," *Ann. Rev. Phys. Chem.*, vol. 55, pp. 585-611 (Jun. 2004).

Mizrahi et al., "Deviations from Kleinman symmetry measured for several simple atoms and molecules," *Phys. Rev. A*, vol. 31, No. 5, pp. 3145-3154 (May 1985).

Mühlschlegel et al., "Resonant Optical Antennas," *Science Magazine*, vol. 308, No. 5728, pp. 1607-1609 (Jun. 2005).

Patra et al., "Image Analysis of Defocused Single-Molecule Images for Three-Dimensional Molecule Orientation Studies," *J. Phys. Chem. A.*, vol. 108, No. 33, pp. 6836-6841 (Jul. 2004).

Patra et al., "Defocused imaging of quantum-dot angular distribution of radiation," *Appl. Phys. Lett.*, vol. 87, pp. 101103-1-101103-3 (Aug. 2005).

Richards et al., "Electromagnetic diffraction in optical systems: II. Structure of the image field in an aplanatic system," *Proc. R. Soc. Lond.*, Series A, vol. 253, No. 1274, pp. 358-379 (Dec. 1959).

Sandeau et al., "Defocused imaging of second harmonic generation from a single nanocrystal," *Optics Express*, vol. 15, No. 24, pp. 16051-16060 (Nov. 2007).

Sönnichsen et al., "Gold Nanorods as Novel Nonbleaching Plasmon-Based Orientation Sensors for Polarized Single-Particle Microscopy," *American Chemical Society*, Nano Lett., vol. 5, No. 2, pp. 301-304 (Dec. 2004).

Török et al., "Electromagnetic diffraction of light focused through a planar interface between materials of mismatched refractive indices: an integral representation," *J Opt. Soc. Am. A*, vol. 12, No. 2, pp. 325-332 (Feb. 1995).

Tripathi et al., "Determination of the second-order nonlinear susceptibility elements of a single nanoparticle using coherent optical microscopy," *J. Phys. B.: At. Mol. Opt. Phys.*, vol. 44, No. 1, pp. 1-6 (Jan. 2011).

van Dijk et al., "Absorption and scattering microscopy of single metal nanoparticles," *Phys. Chem. Chem. Phys.*, vol. 8, pp. 3486-3495 (Jul. 2006).

Yazdanfar et al., "Interferometric second harmonic generation microscopy," *Optics Express*, vol. 12, No. 12, pp. 2739-2745 (Jun. 2004).

\* cited by examiner

SECOND-ORDER NONLINEAR SUSCEPTIBILITY OF A NANOPARTICLE USING COHERENT CONFOCAL MICROSCOPY

The present application is a continuation-in-part of U.S. patent application Ser. No. 12/405,711, filed Mar. 17, 2009, and, like that application, claims priority from provisional application Ser. No. 61/037,419, filed Mar. 18, 2008. Both of the aforementioned applications are hereby incorporated by reference herein.

Portions of this invention were developed with Government support under MURI Grant No. F49620-03-10379, awarded by the US Air Force, and under NSF CAREER Grant No. 0239265, awarded by the National Science Foundation. The Government has certain rights in the invention.

TECHNICAL FIELD OF THE INVENTION

The present invention pertains to optical methods and apparatus for determining characteristics of the susceptibility of a nanoparticle, and, more particularly, to determining both linear and non-linear susceptibility elements.

BACKGROUND OF THE INVENTION

Nanoparticles are currently the subject of intense study as surveyed, for example, in G. Schmid, ed., *Nanoparticles: From Theory to Application* (Wiley, 2004), which is incorporated herein by reference. Applications are as diverse as drug delivery, sensing, bio-imaging and sorbent manufacture. Not least among the interesting properties of nanoparticles are their optical characteristics. The optical attributes of nanoparticles are observed in familiar materials such as opal and stained glass. More recently the optical properties of nanostructures have been exploited in applications such as the construction of metamaterials, discussed by Ziolkowski et al., eds., *Metamaterials: Physics and Engineering Explorations* (Wiley, 2006), and the subwavelength containment of fields using optical antennas, as discussed by Miihlschlegel et al., *Resonant optical antennas, Science,* 308, 1607-1609 (2005). With the increasing use of nanoparticles in optical applications it is desirable to be able to characterize the optical response of a single nanoparticle. This work focuses on the elastic scattering properties of a nanoparticle, as manifested by a wavelength-dependent susceptibility tensor, which expresses the relationship between polarization of the particle and electric fields: linear in the case of polarizability, and to successive orders of the field, when non-linear contributions are considered.

The susceptibility of a nanoparticle is determined both by the constituent material and by the particle size and shape. For purposes of the present description, unless the particular context requires otherwise, the term "nanoparticle" will refer to a scatterer having point-like characteristics, in that its overall dimensions are smaller than the diffraction limit of any radiation used in its characterization. For a known material and geometry, the polarizability may be determined analytically or by computational methods, and so may non-linear terms, in principle. However, small deviations from the specified shape may introduce significant optical changes. See Canfield et al., *Chirality arising from small defects in gold nanoparticle arrays, Opt. Express* 14, 950-955 (2006) for a discussion of related measurements from nanoparticle arrays. It is, therefore, highly desirable that methods be provided for actually measuring terms of the susceptibility using far-field optical measurements. Such methods are provided by the current invention, as discussed below.

To date, limited effort has been placed on determining the elements of the second-order nonlinear susceptibility tensor for individual nanoparticles. Yet, it has been demonstrated with biological samples that the determination of the tensor elements provides additional information about the nanoparticles and may be useful in fields like bioimaging, sensing, drug delivery, and imaging, more generally.

The measurement scheme of the present invention is based on improvements to a coherent confocal microscope. Coherent microscopes use interference with a reference beam to holographically record data and hence acquire information regarding the phase of the measured field. While coherent microscopy predates the invention of the laser, modern bright and broadband sources have made spectrally-sensitive coherent microscopy a practical methodology. This is evidenced by the popularity of techniques such as optical coherence tomography (OCT).

In addition to collecting phase-sensitive data, a coherent microscope has the advantage of high sensitivity when compared to a traditional intensity-based system. As a result, coherent microscopy is suitable for true nanoimaging, as demonstrated by results such as the interferometric detection of single viruses and gold particles as small as 5 nm, as reported by Ignatovich et al., *Real-time and background-free detection of nanoscale particles, Phys. Rev. Lett.,* 96, article no. 013,901 (2006).

In coherent microscopy the optical source is usually split into a reference field and a field that is used to illuminate the sample. The light returned from the sample is combined with the reference field and the interferometric features in the data are used for image formation. To exhibit interference the returned light must be coherent with the reference field and at the same frequency. This means that potentially useful signals from a nanoparticle, such as Raman-scattered, higher-harmonic and/or fluorescent light, are not detected. In more generalized coherent microscopy, the reference field may be light that is derived coherently from the optical source used to illuminate the sample.

Second-harmonic generation (SHG) is a coherent second-order non-linear optical process which produces an optical field at twice the frequency of the input (pump) field; this process occurs only in noncentrosymmetric material systems. The second-order nonlinear susceptibility that describes the generation of the SHG signal depends on the electronic configurations, molecular structures and alignments, and local morphologies of the system. As a result, SHG has been successfully used to investigate the local molecular alignment and/or the structure in a wide variety of materials including biological tissues, organic and inorganic crystals, molecular materials, and surfaces and interfaces. SHG has also been used to characterize individual nanoparticles, as discussed, for example, in Sandeau et al., *Defocused imaging of second harmonic generation from a single nanocrystal, Opt. Express,* 15, 16051 (2007), which is incorporated herein by reference. In one study, the orientation and the crystalline nature of the individual organic nanocrystals were inferred from the SHG signal together with the two-photon excited fluorescence, reported by Brasselet et al., *In-situ diagnostics of the crystalline nature of single organic nanocrystals by nonlinear microscopy, Phys. Rev. Lett.,* 22, 207401 (2004), which is also incorporated herein by reference. In another study, three-dimensional orientation of the individual nanocrystals was determined by imaging the emitted SHG signal using a defocused imaging system Traditional microscopy and spectroscopy usually involve the formation of a scalar image on spatial and/or spectral axes. While this image is immediately useful in many applications, it is possible to design sensing systems that form non-scalar images and/or exploit less obvious relationships between the collected data and the imaged objects. A comprehensive discussion is provided by Barrett et al., *Foundations of Image Science* (Wiley-Interscience, 2003), which is incorporated herein by reference. For example, many modern microscopy and imaging systems collect images as a function of polarization state and/or scattering angle. Additionally, in some applications the object can be represented by a small number of parameters which are estimated from the data with very high precision. In single molecule microscopy, the a priori knowledge that the object can be parameterized by the molecule location allows the molecule to be localized with a precision orders of magnitude better than the diffraction limit.

SUMMARY OF CERTAIN EMBODIMENTS OF THE INVENTION

In accordance with preferred embodiments of the present invention, a method is provided for measuring at least one element of a susceptibility tensor of a nanoparticle. The methods have steps of:
  a. illuminating the nanoparticle via a first vector beam shaper with an illuminating electromagnetic wave;
  b. coherently detecting light scattered by the nanoparticle and propagated through a vector analyzer to generate a detected signal; and
  c. performing an inversion of the detected signal based on a comparison of the detected signal to data predicted from a forward scattering model; and
  d. estimating at least one element of the susceptibility tensor of at least one order based on the inversion.

In accordance with further embodiments of the invention, the step of performing an inversion may be subject to specified symmetry assumptions. Moreover, performing the inversion may include minimizing a specified cost function.

The step of coherently detecting light scattered by the nanoparticle may include detection relative to a reference beam identical to that of the illuminating electromagnetic wave, or relative to a reference beam that is coherently related to the illuminating electromagnetic wave. In particular, the reference beam may be generated from the illuminating electromagnetic wave as a second harmonic. The inversion may be subject to an assumption of Kleiman symmetry of the nonlinear susceptibility tensor.

In an alternative embodiment of the invention, the aforesaid methods may have a further step of spectrally resolving the detected light. The illuminating radiation may be scanned in a plane transverse to the illumination direction. The vector analyzer may, in some cases, be identical to the vector beam shaper.

In other embodiments of the present invention, there may be a further step that entails varying a physical parameter of an environment in which the nanoparticle is disposed. Moreover, the step of estimating at least one element of at least one order of the nanoparticle susceptibility may include minimizing a cost function based on a norm relating the detected signal to an estimate.

In accordance with another aspect of the present invention, an improvement to an optical coherence microscope is provided for estimating linear polarizability of a particle. The improvement has a vector beam shaper disposed within the illuminating beam.

In accordance with yet another aspect of the present invention, a computer program product is provided for use on a computer system for calculating, with respect to a nanoparticle characterized by a polarizabilty, the polarizability of the nanoparticle as a function of wavelength. The computer program product has a computer usable medium containing computer readable program code that includes:
  a. program code for generating a forward scattering model based on forward scattering by a point source;
  b. program code for receiving a signal based on coherent detection of light scattered by the nanoparticle and propogated through a vector analyzer;
  c. program code for performing an inversion of the detected signal based on a comparison of the detected signal to data predicted from a forward scattering model; and
  d. program code for estimating nanoparticle polarizability based on the inversion.

DESCRIPTION OF THE FIGURES

The foregoing features of the invention will be more readily understood by reference to the following detailed description, taken with reference to the accompanying drawings, in which:

FIG. 5A plots the Euclidean norm of the error in the retrieved values, and FIG. 5B plots the position as a function of the signal-to-noise ratio, employing methods in accordance with the present invention.

DESCRIPTION OF SPECIFIC EMBODIMENTS OF THE INVENTION

Definition. As used in this description and the accompanying claims, the following term shall have the meaning indicated, unless the context otherwise requires:

An "analyzer" is any optical element that breaks the symmetry of an optical system with respect to the vector orientation of an optical field in a plane transverse to its propagation direction. Examples include both static and dynamic polarizers, whether homogeneous or patterned.

In accordance with certain embodiments of the present invention, methods are taught for determining both the position and the elements of the second-order susceptibility tensor of individual nanoparticles. These methods employ a coherent confocal microscope and exploit the fact that SHG is a coherent process so that the phase and the amplitude of the field may be obtained interferometrically. It is assumed that the particle is pointlike, that is, its structure is unresolvable on the scale of the wavelength of light, and that the particle can be characterized by a single second-order susceptibility tensor. While analysis of large particles is within the scope of the present invention, a more complicated model is employed, as taught in Davis et al., *Robust determination of the anisotropic polarizability of nanoparticles using coherent confocal microscopy, J. Opt. Soc. Am. A*, 25, pp. 2102-13 (2008), which is incorporated herein by reference. The framework taught in the present application is modular and such modifications may be applied by persons of ordinary skill in the art.

It is assumed, for heuristic purposes, that the particle is fixed in position and well isolated from other particles such that there is no inter-particle interaction, and that the optical field used to characterize the particle does not interact with neighboring particles. In a general setting, there are not enough data available to solve for all elements of the nonlinear susceptibility simultaneously. However, it is often possible to invoke symmetries of the tensor to reduce the number of free variables and resolve the remaining elements. Kleinman symmetry may be invoked for nondispersive nonabsorbing media, as taught, for example, by Dailey et al., *The general failure of Kleinman symmetry in practical nonlinear optical applications, Chem. Phys. Letters*, 390, pp. 8-13 (2004), which is incorporated herein by reference. Then, the methods described herein may be used to infer the position and extract all elements of the second-order susceptibility. In the case of failure of the Kleinman symmetry, other symmetries may be invoked to similar ends, with reference, again, to Dailey (2004). Since, in practice, the overall scale of the data is not known precisely, the susceptibility tensor elements are estimated up to a constant scaling factor. In practice, nanoparticles are typically on substrates; the retrieved susceptibility derived in accordance with methods described herein is then the effective susceptibility that includes the effect of the substrate-particle interaction. The bare particle polarizability can then be inferred from the effective polarizability.

In the following section the forward model for the coherent confocal microscope is derived. Embodiments of the invention used for estimating the susceptability are given in the section entitled Inverse Problem, i.e., the inverse problem is solved. Methods in accordance with the invention are then demonstrated and characterized using numerical experiments.

Figure 1:
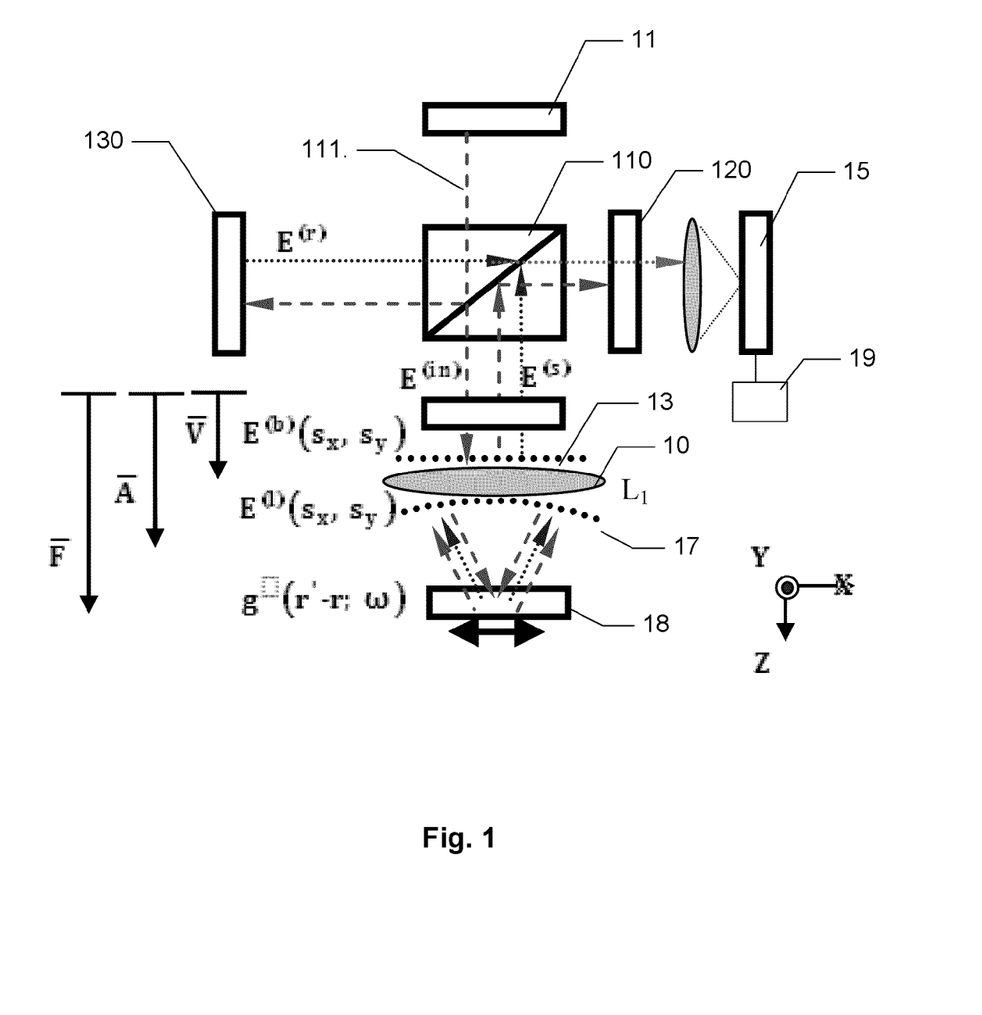
FIG. 1 is a schematic depiction of a coherent confocal system in accordance with preferred embodiments of the present invention, including fields and tensor operators used in the model derivation.

FIG. 1 shows a basic system diagram in accordance with embodiments of the present invention. An input beam 111 with fundamental frequency $\omega$ (designated by dashed arrows) is generated by source 11 and passes through a beam splitter 110. Part of the beam passes through a vector beam shaper 12, which imparts a specified phase and intensity distribution to input beam 111, thereby giving rise to a field $E^{(b)}$ at the entrance pupil 113 of a lens 10 of high numerical aperture (NA). The beam is then refracted by lens 10 which results in the field $E^{(l)}$ at exit pupil 17 of the lens, and a field g in the focal volume. The sample 18 consists of a substrate supporting the nanoparticle to be characterized. As mentioned earlier, the substrate can have more than one nanoparticle; however, these nanoparticles should be sparsely distributed so that the focused beam interacts with only the nanoparticle to be characterized. The interaction of the nanoparticle with the focused optical field generates the backscattered signal $E^{(s)}$ which consists of the optical field at both the fundamental ($\omega$) and the second harmonic ($2\omega$, designated in FIG. 1 by dotted arrows) frequencies. This signal then propagates back through lens 10 and is combined with a reference SHG signal, $E^{(r)}(2\omega)$, at beam splitter 110. An SHG filter 120 in the signal path ensures that only the second-harmonic signal is recorded at detector 15. The reference SHG signal can be generated using a nonlinear crystal 130 with a large second-order susceptibility such as beta-barium borate (BBO) or lithium triborate (LBO), provided by way of example only, and without limitation. It should also be noted that the reference SHG signal must be generated from the illuminating optical source in order to ensure that the reference field is coherent with the SHG signal backscattered from the nanoparticle, as demonstrated by Yazdanfar et al., *Interferometric second harmonic generation microscopy, Opt. Express*, 12, pp. 2739-45 (2004), which is incorporated herein by reference. It is to be understood that the overall configuration in which the sample return beam is combined with a reference beam may be referred to herein as an interferometer, and that interferometric configurations other than those shown are similarly within the scope of the present invention.

Forward Model

The nanoparticle position and susceptability are determined by selecting values that best explain the measured data. In order to do this, the instrument must be thoroughly modeled. This section describes such a model, which is generated in process 21 of FIG. 2, following the coherent microscope treatment presented in Davis et al., *Nonparaxial vector-field modeling of optical coherence tomography and interferometric synthetic aperture microscopy, J. Opt. Soc. Am.* 24, pp. 2527-42 (2007), which is incorporated herein by reference and referred to hereinafter as "Davis 2007."

The intensity measured at detector 15 is a function of both the position of the geometrical focus r=(x, y, z), and the second-harmonic angular frequency $2\omega$), and can be written as $$I(r;2\omega) = \langle |E^{(r)}(2\omega)|^2 + 2Re\{S(r;2\omega)\} + |E^{(s)}(r;2\omega)|^2 \rangle, \quad (1)$$

where $\langle \ldots \rangle$ represents a time-averaging operation. In Eq. (1), the first term depends only on the reference signal; assuming a plane wave reference signal the dependence on r can be removed. The third term, which is the autocorrelation term, is typically very small and can usually be neglected. The interferometric cross term, defined as $$S(r;2\omega) = \langle \{E^{(r)}(2\omega)\}^\dagger E^{(s)}(r;2\omega) \rangle, \quad (2)$$

can be recovered from its measured real part, $Re\{S(r; 2\omega)\}$, using the Hilbert transform, where † represents the Hermitian transpose operator. Note that the application of the Hilbert transform in retrieving the complex field is applicable when the data is collected over a range of frequencies; alternatively, if the measurements are carried out at a single frequency, phase-shifting interferometry may also be used, within the scope of the present invention. However, the scope of the claimed invention encompasses any method used to retrieve the complex field.

To determine the backscattered field $E^{(s)}$ (r; $2\omega$), a forward model is developed for the field from the incident field, through the optical system, to the interaction with the sample, and back out. The beam delivered by the source onto vector beam shaper 12 will be designated herein as $E^{(in)}(\omega)$. It is converted to the field $E^{b)}(s_x,s_y;\omega)$ on the entrance pupil of the lens by the vector beam shaper 12, such that $$E^{b)}(s_x,s_y;\omega) = \overline{V}(s_x,s_y)E^{(in)}(\omega), \quad (3)$$

where $s_x$ and $s_y$ are the components of the unit vector directed from a point on the exit pupil to the geometrical focus, which can be mapped to a corresponding point on the entrance pupil by ray tracing, where $\overline{V}(s_x,s_y)$ is a tensor operator describing the operation of the vector beam shaper 12. Assuming an aplanatic lens obeying the sine condition and the intensity law, as described in Novotny et al., *Principles of Nano-Optics*, (2007), incorporated herein by reference, the refracting action of the lens can be written as $$E^{l)}(s_x,s_y;\omega)) = \overline{A}(s_x,s_y)E^{(in)}(\omega), \quad (4)$$

where the tensor $\bar{A}$ includes both the effect of vector beam shaper 12 and refraction by lens 10. The field at an arbitrary point r' is calculated as $$g(r'-r;\omega) = \frac{k}{2\pi i} \int ds_x ds_y \frac{\bar{A}(s_x, s_y)E^{(in)}(\omega)}{s_z(s_x, s_y)} e^{iks \cdot (r'-r)} \quad (5)$$
$$= \bar{F}(r'-r;\omega)E^{(in)}(\omega)$$

where F is a tensor that includes the effect of vector beam shaper 12 and the lens 10. The parameter $s_z$, in free space, is related to $s_x$ and $s_y$ through the standard relation $s_z = \sqrt{1 - s_x^2 - s_y^2}$. The angular spectrum representation approach outlined here can also be modified, within the scope of the present invention, to allow for situations where the field is focused onto a sample with background index mismatch.

Assuming that the nanoparticle is at a position $r^{(p)}$ (p represents the position of the nanoparticle) and its effective 3×6 susceptibility tensor in contracted notation, i.e., the second-order susceptibility tensor under permutation symmetry, is represented by d, the resultant second-harmonic polarization may be written as $$P(2\omega) = d \begin{bmatrix} g_x^2(r^{(p)}-r;\omega) \\ g_y^2(r^{(p)}-r;\omega) \\ g_z^2(r^{(p)}-r;\omega) \\ g_y(r^{(p)}-r;\omega)g_z(r^{(p)}-r;\omega) \\ g_x(r^{(p)}-r;\omega)g_z(r^{(p)}-r;\omega) \\ g_y(r^{(p)}-r;\omega)g_x(r^{(p)}-r;\omega) \end{bmatrix} = d \begin{bmatrix} e_1 \\ e_2 \\ e_3 \\ e_4 e_5 \\ e_6 \end{bmatrix}, \quad (6)$$

where $g_x$, $g_y$ and $g_z$ are the x, y and z components of the focal field g, and $e_i$ is shorthand for the ith-row element of the 1×6 vector of products of the elements of g. The amplitude of the field resulting from this induced second-harmonic polarization is proportional to $k^2 P(2\omega)$. This field propagates back through lens 10. By reciprocity, this operation can be described by $\bar{F}^T(2\omega)$, where T refers to the transpose of the operator. Hence, the backscattered second-harmonic field can be written as $$E^{(s)}(r;2\omega) \propto k^2 \bar{F}^T(r^{(p)}-r;2\omega)P(2\omega) \quad (7)$$

It should be noted that $\bar{F}$ implicitly includes the dyadic Green's function, which is frequency dependent. There is a backscattered fundamental field as well; however, it is neglected in the analysis, since it is filtered out. The backscattered field then interferes with the reference field. Using Eq. (2), the complex field can be written as $$S(r;2\omega) \propto k^2 \langle [E^{(r)}(2\omega)]^\dagger \bar{F}^T(r^{(p)}-r;2\omega)P(2\omega) \rangle \quad (8)$$

Thus, an image may be acquired by fixing the focal plane at z=0 and scanning the stage in two dimensions in (x,y). The received complex field, using the Einstein summation notation, can be written as $$S(x,y;2\omega) \propto d_{ij}(\omega) h_{ij}(x-x^{(p)}, y-y^{(p)}; z^{(p)}, 2\omega), \quad (9)$$

where $h_{ij}$ are optical response functions (ORFS) which help discriminate the output signal due to each susceptibility element and are defined as $$h_{ij}(x,y;z^{(p)},2\omega) = k^2 E_l^{(r)*}(2\omega) F_{il}(-x,-y;z^{(p)},2\omega) e_j. \quad (10)$$

In Eq. (10) the Einstein summation notation has again been used, and * represents the complex conjugate. Also, the subscripts i, l=1, 2, 3, and j=1, . . . , 6 represent corresponding elements of the parent tensor/vector. For example, $F_{12}$ represents the element of the first row and second column of the operator $\bar{F}$. As Eq. (6) shows, $e_j$s are functions of the nanoparticle position. From Eq. (9), one sees that although the backscattered second-harmonic signal is a second-order function of the input field (through $e_j$), it is linearly dependent on the susceptibility elements.

The ORFs defined in Eq. (10) are general. Since it is not possible to solve for the elements of the susceptibility in the general case, some prior constraint must be applied in accordance with the invention. Here, the Kleinman symmetry is invoked as an example, applicable when d is taken to have the following form:

$$d = \begin{bmatrix} d_{11} & d_{12} & d_{13} & d_{14} & d_{15} & d_{16} \\ d_{16} & d_{22} & d_{23} & d_{24} & d_{14} & d_{12} \\ d_{15} & d_{23} & d_{33} & d_{23} & d_{13} & d_{14} \end{bmatrix}. \quad (11)$$

Eqn. (9) constitutes the forward model and can be used to predict the recorded signal when both the position $r^{(p)}$ and the effective second-order susceptibility matrix d of the nanoparticle are known.

Figure 2:
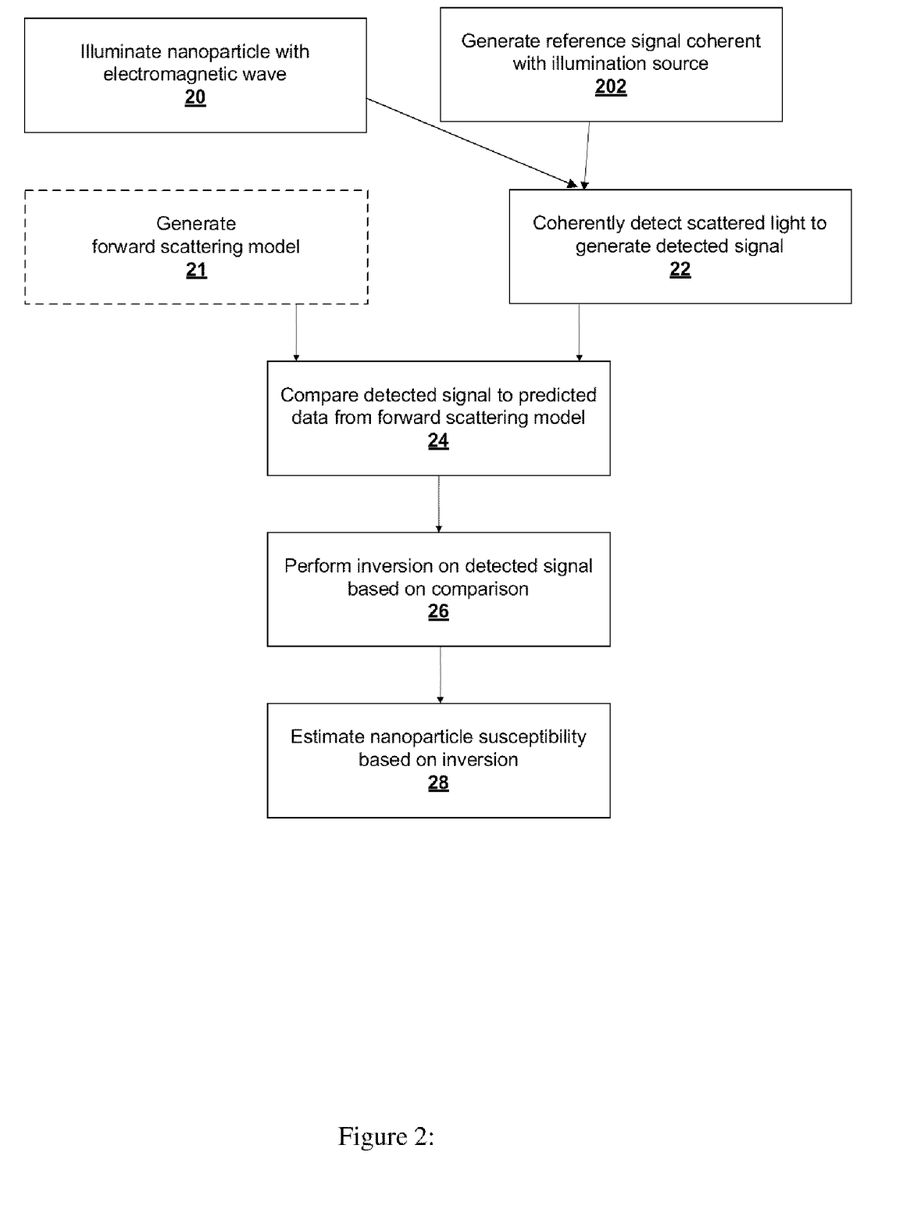
FIG. 2 is a flow chart of a method for measuring elements of the susceptibility of a nanoparticle using the coherent confocal system of FIG. 1 in accordance with an embodiment of the present invention.

Applying a coherence microscopy apparatus as described above with reference to FIG. 1, and referring now to the process flow diagram of FIG. 2, in process 20 of FIG. 2 an illuminating field is used to illuminate the nanoparticle comprising sample 18 and to generate a reference signal coherent with the illuminating source 20, either at the same frequency (or set of frequencies) as the illuminating source, or at a harmonic, as in the case of measurement of the second-order non-linear susceptibility. In process 22 of FIG. 2, the scattered field is combined with the reference field by an interferometer, designated generally by numeral 100, and the collected field is averaged at detector 15. Data from the detector is processed by a processor 19 according to the techniques described in detail below. In some embodiments, the processor may perform control functions, such as directing the physical displacement of sample 18 during scanning.

Inverse Problem

With a forward model formulated, the inverse problem can be addressed. Solution of the inverse problem provides for estimating the nanoparticle parameters from the collected data. The inverse problem can be solved by comparing, in process 24 of FIG. 2, the observed data to data predicted using the forward model and a given set of nanoparticle parameters.

To estimate the nanoparticle parameters, namely the susceptibility elements and the position of the particle, from the collected data, the inverse problem needs to be solved. This is achieved by searching for the set of parameters that lead to the smallest deviation between the observed data and that predicted from the forward model. There are several different quantitative metrics to estimate the deviation. For heuristic purposes, and without limitation of the scope of the present invention, the Euclidean norm is used, thus the cost function assumes the form:

$$C(d, r^{(p)}; 2\omega) = \|S(\rho 2\omega) - d_{ij}(\omega) h_{ij}(x-x^{(p)}, y-y^{(p)}; z^{(p)}, 2\omega)\|. \quad (12)$$

The Euclidian norm chosen in Eqn. (12) is consistent with a Gaussian noise model characteristic of interferometer measurements dominated by the noise from the reference beam and/or thermal detector noise. The information about the position and the susceptibility of the nanoparticle is encoded in the recorded signal through the ORFs in Eq. (10), therefore successful retrieval of these parameters, as in any coding/decoding process, depends on the ability of ORFs to sufficiently encode each susceptibility element onto the recorded data. Specifically, the ORFs are required to each be distinct and non-negligible. Furthermore, since the ORFs are dependent on the input field in the focal region, successful use of this technique requires that an appropriate beam type be used. For example, the focal field for a Gaussian beam contains a negligibly small field of z polarization. As a result, for the Gaussian beam, several ORFs, such as $h_{13}$ are expected to be negligible as they depend on either the z or a product of the z- and the x- or the y-polarized field in the focal region. In contrast, a strongly focused radial vector beam, a beam with polarization distribution that is radially pointing outward from the beam center at each point, is also not expected to be a good choice for this technique because under very strong focusing a radial vector beam provides a strong z-polarized field at the expense of the x- and the y-polarized field. In this case, ORFs such as $h_{11}$ and $h_{12}$ are expected to be negligible as they depend either on the x or the y, or a product of the z- with the x- or the y-polarized field.

Figure 3:
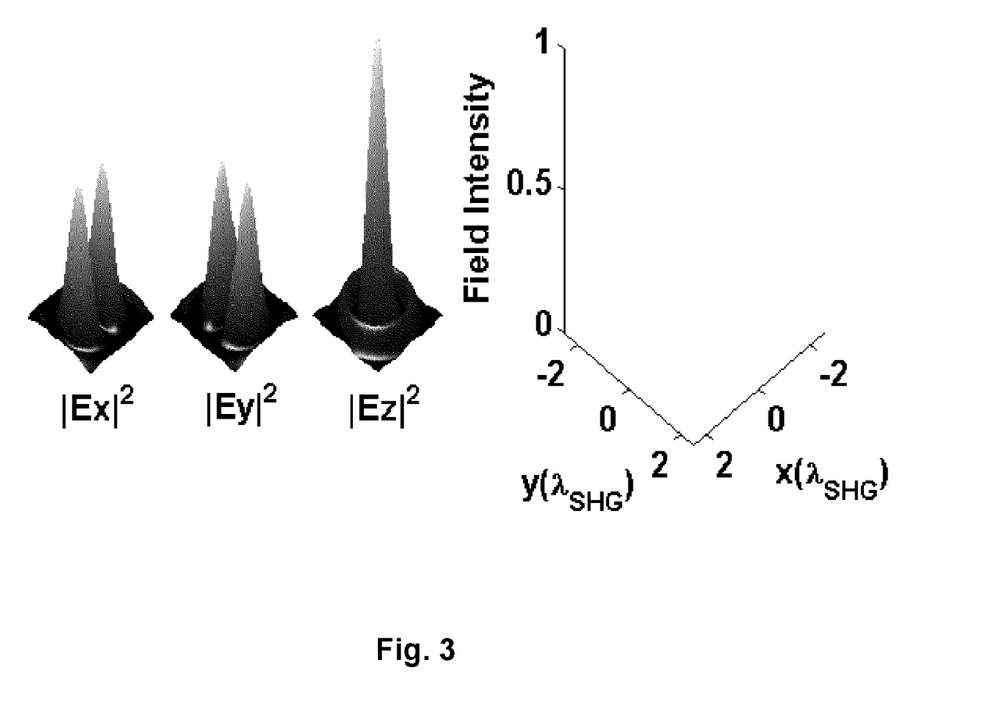
FIG. 3 depicts the intensity of each polarization component at the focal plane with the input beam and the lens parameters specified in the text. The intensities are normalized by the maximum intensity across all polarizations and all positions.
Figure 4:
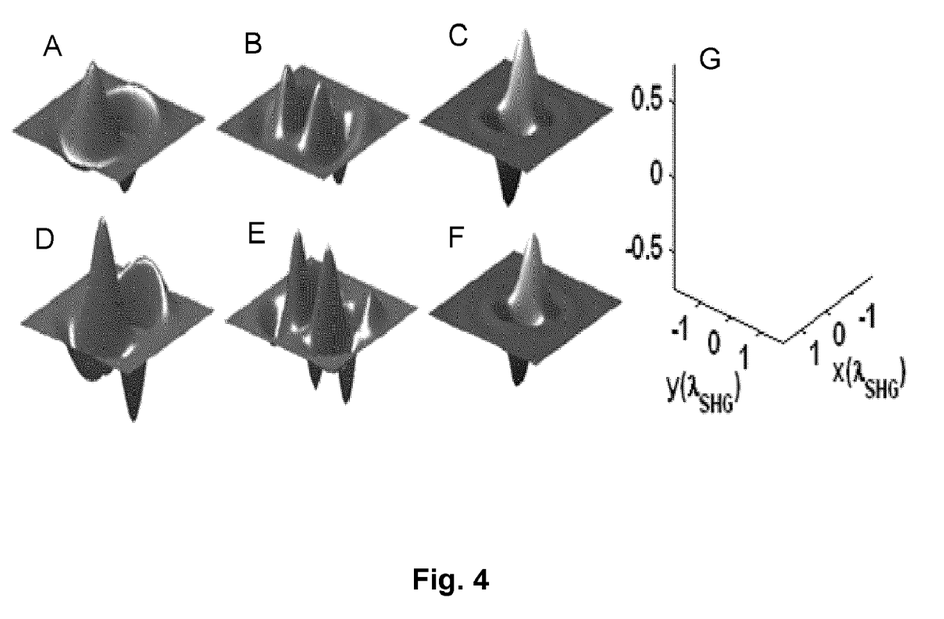
FIGS. 4A-4C show the real parts of the first three spatial domain ORFs.
FIGS. 4D-4F show the corresponding imaginary parts.
FIG. 4G shows the scales used for these plots, with the axes labeled in units of wavelength and the ORF values normalized by the maximum value across all ORFs.

In the simulation described below, a modified radial beam is used that is focused using a 0.8 numerical-aperture lens. The vector beam generator used in the simulation blocks the central portion of the input beam and rotates the polarization at other points by an angle equal to the azimuthal angle of the point. Example techniques to generate such beams include the use of spiral phase delay plates, graded transmission filter, and spatial light modulators. The resulting focal field distribution has comparable x, y, and z polarization field strengths (see FIG. 3) which cannot be achieved by using a uniformly polarized Gaussian beam. FIG. 4 shows the real and imaginary components of the first three of the ten independent spatial domain ORFs, using the modified radial beam, when the reference field is linearly polarized along the x axis.

In FIG. 4, the real (FIGS. 4A-4C), and the imaginary (FIGS. 4D-4F parts of the first three (of ten) spatial domain ORFs are shown: $h_{11}$, $h_{12}$, $h_{13}$ for a radial vector beam at a defocus of $0.125\lambda_{SHG}$, where $\lambda_{SHG}=2\pi c/2\omega$). These ORFs are dependent on the input beam type as well as the amount of defocus, and encode the position and the susceptibility information of the nanoparticle onto the recorded signal. Thus, these ORFs can also be thought of as the basis elements, albeit non-orthogonal, onto which the measured field can be decomposed. The coefficients of the decomposition provide the ten independent elements of the second-order susceptibility tensor under the permutation and Kleinman symmetry. FIG. 4G shows the scales used for these plots. Here, the axes have been labeled in the units of wavelength and the ORF values have been normalized by the maximum value across all ORFs.

Simulations

Numerical simulations now demonstrate the performance of one of the embodiments of the method described in the present invention. In the simulations, the nanoparticle parameters were generated randomly. One set of position values is shown below:

$$r^{(p)} = \lambda_{SHG}[-0.0139 -0.1774 -0.0241]^T. \quad (13)$$

The Kleinman symmetry assumes (optical) transparency, and, as such, the susceptibility elements should be real. An example of this is shown below where the values have been normalized by the maximum value.

$$d = \begin{bmatrix} 0.8274 & 0.5416 & 0.2956 & 0.3078 & 1.0000 & 0.7854 \\ 0.7854 & 0.6721 & 0.5913 & 0.7503 & 0.0378 & 0.5416 \\ 1.0000 & 0.7503 & 0.1569 & 0.5913 & 0.2956 & 0.0378 \end{bmatrix}. \quad (14)$$

The position $r^{(p)}$ and the contracted susceptibility matrix d were then used in Eq. (9) to generate the synthetic data. It consisted of a 2-D complex-field distribution $S(x, y; 2\omega)$. In addition, since the data collected in actual measurements are never noise free, complex random Gaussian noise was added. To generate an image with a given value of signal to noise ratio (SNR), for each pixel, the noise level is randomly chosen from a Gaussian distribution with mean and variance defined by both the signal level at that pixel and the required SNR. Specifically, the real and the imaginary parts of the complex noise are generated independently from a Gaussian distribution whose variance is equal to the half of the ratio of the signal power to the SNR. The power at each pixel is calculated as the square of the amplitude of the complex signal at that pixel.

To solve the inverse problem, the Nelder-Mead algorithm was applied over the particle position through the fminsearch function in MATLAB. The initialization point for the algorithm was randomly generated using the rand function in MATLAB with a range of $1.5\lambda_{SHG}$ in the x- and y-direction centered on the origin. During each iteration, the corresponding elements of the susceptibility were calculated using matrix inversion of the data in Eq. (9). Without any restriction, fminsearch will converge to complex values. However, requiring the susceptibility to be real at the start of the optimization procedure derails convergence as this constraint introduces discontinuity in the objective function whereas fminsearch assumes continuous objective function. This problem was circumvented by permitting complex values at the beginning of the optimization procedure and restricting the susceptibility to be real once a minimum is approached.

For an SNR of 25 dB, the following values of position $$\hat{r} = \lambda_{SHG}[-0.0141 -0.1767 -0.0239]^T. \quad (15)$$

and susceptibility elements $$\hat{d} = \begin{bmatrix} 0.827423 & 0.5325 & 0.2972 & 0.0342 & 1.0000 & 0.7813 \\ 0.7813 & 0.6690 & 0.5867 & 0.7451 & 0.0342 & 0.5325 \\ 1.0000 & 0.7451 & 0.1518 & 0.5867 & 0.2972\nu & 0.0342 \end{bmatrix} \quad (16)$$

were estimated. Again retrieved values have been normalized by the maximum real part. In practical systems the absolute scale of the data will not be known precisely hence the normalization is for comparison purposes so the susceptibility is estimated to within a constant scaling. It should be observed that the estimated value of the position closely matches the expected value [Eq. (13)] despite the noise. Also, comparing the elements of the matrix $\hat{d}$ with the elements of the matrix d, it is apparent that the values closely match despite the noise. It should be noted that in a physical experiment, the deduced susceptibility would be determined in the macroscopic (laboratory) reference frame. To correlate these values to the crystal structure, one will need to supplement retrieved values with knowledge of the orientation of the emission dipole (multipole) of the particle which can be obtained from techniques like defocused imaging, as taught, for example, by Sandeau (2007).

Figure 5:
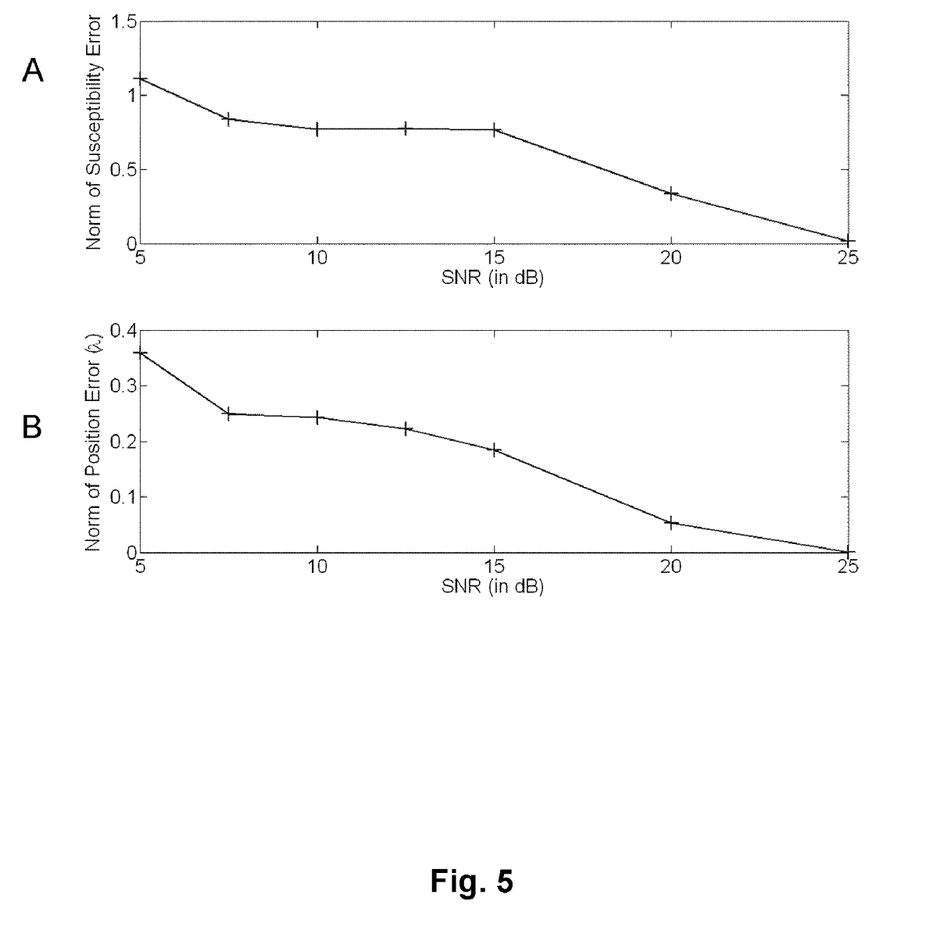

The effect of the noise on the accuracy of the retrieved position and susceptibility is shown in FIGS. 5A and 5B. For each data point shown, numerical experiments were run ten times at a constant noise level and with a separate set of randomly generated nanoparticle parameters. The particle was restricted to the focal plane for all calculations. The error values shown are the average of the ten error values for each point. The confocal scanning step size in the transverse direction (along x- or y-) and in the axial direction was $0.125\lambda_{SHG}$ and $0.25\lambda_{SHG}$, respectively. FIG. 5A shows the norm of the error in the susceptibility elements. Similarly, FIG. 5B shows the Euclidian norm of the error in position $\hat{r}^{(p)}-r^{(p)}$ as a function of the SNR. We observe the intuitive result that as the SNR is increased the error decreases. Since only 10 of the 18 elements are independent, to calculate the norm, a vector of these 10 elements was constructed and the corresponding Euclidian norm was calculated. It again shows an improvement in the retrieval accuracy as the noise level is decreased. Although, in these calculations, the particle is assumed to be in the focal plane (i.e., z=0), methods in accordance with the invention described herein allow for the position and susceptibility of the particle to be retrieved even if the particle is located in any other plane.

The present invention may be embodied in any number of instrument modalities. In alternative embodiments, the disclosed methods for evaluating nanoparticle polarizability may be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product). These and other variations and modifications are within the scope of the present invention as defined in any appended claims.

We claim:

1. A method for measuring at least one element of a susceptibility tensor of at least one order pertaining to a nanoparticle:
   a. illuminating the nanoparticle via a first vector beam shaper with an illuminating electromagnetic wave;
   b. coherently detecting light scattered by the nanoparticle and propagated through a vector analyzer to generate a detected signal, wherein the vector analyzer is a vector beam shaper;
   c. employing a computer system to perform an inversion of the detected signal based on a comparison of the detected signal to data predicted from a forward scattering model; and
   d. estimating at least one element of at least one order of the susceptibility, based on the inversion.

2. The method of claim 1, wherein the step of performing an inversion is subject to specified symmetry assumptions.

3. The method of claim 1, wherein the step of performing an inversion includes minimizing a specified cost function.

4. The method of claim 1, wherein the step of coherently detecting light scattered by the nanoparticle comprises detection relative to a reference beam identical to that of the illuminating electromagnetic wave.

5. The method of claim 1, wherein the step of coherently detecting light scattered by the nanoparticle comprises detection relative to a reference beam coherently related to that of the illuminating electromagnetic wave.

6. The method of claim 5, wherein the reference beam is generated from the illuminating electromagnetic wave as a second harmonic.

7. A method in accordance with claim 6, wherein the step of performing an inversion is subject to Kleinman symmetry.

8. A method in accordance with claim 1, further comprising a step of spectrally resolving the detected light.

9. A method in accordance with claim 1, further comprising scanning the illuminating radiation in a plane transverse to the illuminating direction.

10. A method in accordance with claim 1, wherein the vector analyzer is identical to the vector beam shaper.

11. A method in accordance with claim 1, further comprising varying a physical parameter on an environment in which the nanoparticle is disposed.

12. A method in accordance with claim 1, wherein the step of estimating at least one element of at least one order of the susceptibility includes minimizing a cost function based on a norm relating the detected signal to an estimate.

13. A method in accordance with claim 1, further comprising a step of spectrally resolving the detected light.

14. A computer program product for use on a computer system for calculating, with respect to a nanoparticle characterized by a susceptibility, one or more elements of a susceptibility tensor, the computer program product comprising a computer usable tangible medium having computer readable program code fixed thereon, the
   computer readable program code including:
   a. program code for generating a forward scattering model based on forward scattering by a point source;
   b. program code for receiving a signal based on coherent detection of light scattered by the nanoparticle and propagated through a vector analyzer, wherein the vector analyzer is a vector beam shaper;
   c. program code for performing an inversion of the detected signal based on a comparison of the detected signal to data predicted from a forward scattering model; and
   d. program code for estimating nanoparticle polarizability based on the inversion.

* * * * *